United States Patent [19]
Chen

[11] Patent Number: 5,273,538
[45] Date of Patent: Dec. 28, 1993

[54] AUTOMATICALLY BLOCKED SAFETY SYRINGE WITH GREATLY UNALIGNED BLOCKING BULB

[76] Inventor: Long-Hsiung Chen, c/o Hung Hsing Patent Service Center P.O. Box 55-1670, Taipei (10477), Taiwan

[21] Appl. No.: 19,609

[22] Filed: Feb. 19, 1993

Related U.S. Application Data

[63] Continuation-in-part of Ser. No. 983,144, Nov. 30, 1992, Pat. No. 5,205,826.

[51] Int. Cl.$^5$ ............................................. A61M 5/00
[52] U.S. Cl. ...................................... 604/110; 604/195
[58] Field of Search ............ 604/110, 187, 195, 218, 604/220, 228

[56] References Cited

U.S. PATENT DOCUMENTS

| | | | |
|---|---|---|---|
| 4,804,370 | 2/1989 | Haber et al. | 604/110 |
| 5,104,378 | 4/1992 | Haber et al. | 604/110 |

*Primary Examiner*—John D. Yasko

[57] ABSTRACT

A safety syringe includes a hollow needle for injection use preliminarily held in a rigid blocking bulb generally conical shaped or truncated-cone shaped having an elongate stem portion protruding rearwardly from the bulb embedded in a rear bulb socket perpendicularly formed in a flexible plug inserted in a front portion of the syringe having a needle head portion formed on a rear portion of the needle, and a plunger slidably held in the syringe for boosting a liquid medicine in the syringe to be injected into a patient through the hollow needle having a needle-head socket recessed in the plunger to be engageable with the needle head portion to drive and move the rigid blocking bulb frontwardly into a front bulb socket which is normally inclinedly formed in the flexible plug and will be operatively biased perpendicularly in the plug when almost exhausting the liquid in the syringe when finishing the injection, whereby upon a retraction of the plunger and the needle coupled to the plunger rearwardly into the syringe, the elongate stem portion of the rigid bulb will be greatly obliquely biased in a larger angle by the front bulb socket of the plug to be much inclinedly positioned for efficiently blocking an outward protruding of the needle retracted in the syringe for really preventing an injury or infectious contamination to the surroundings as caused by the needle.

4 Claims, 3 Drawing Sheets

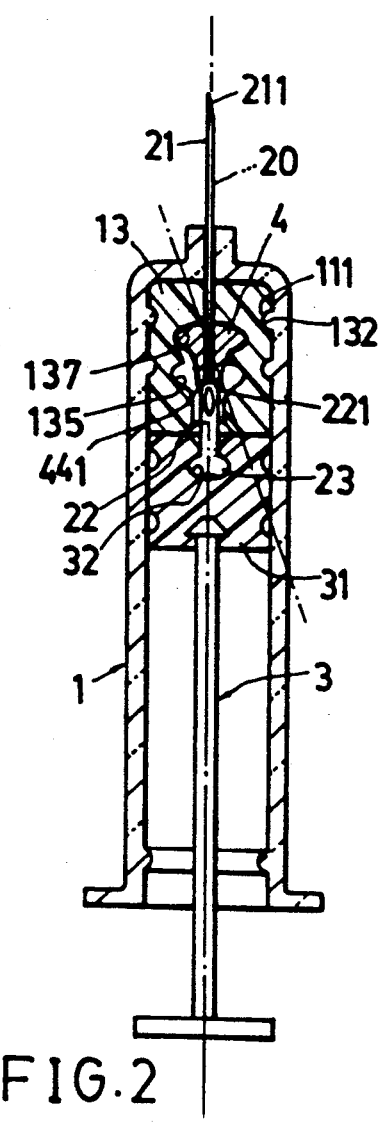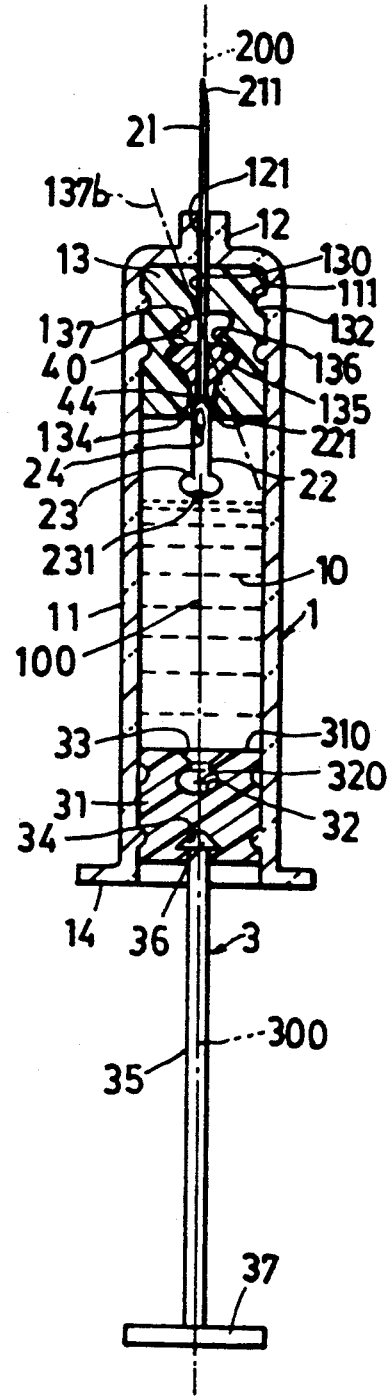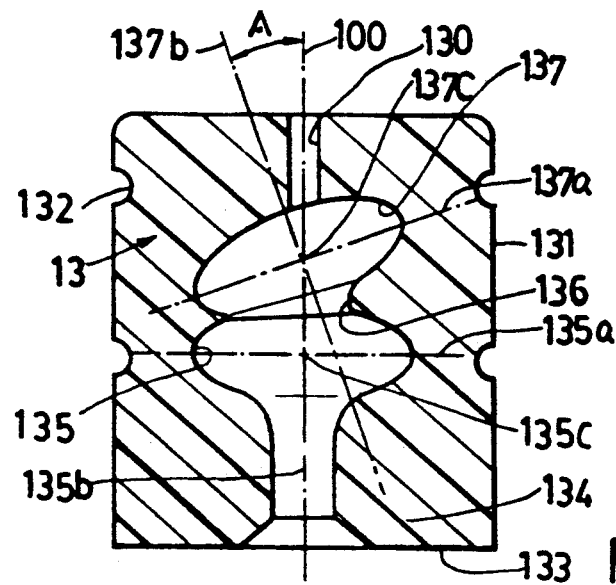
FIG.2
FIG.1
FIG.1A

AUTOMATICALLY BLOCKED SAFETY SYRINGE WITH GREATLY UNALIGNED BLOCKING BULB

BACKGROUND OF THE INVENTION

This application is a continuation-in-part of U.S. patent application Ser. No. 07/983,144 filed Nov. 30, 1992 now U.S. Pat. No. 5,205,826 by the same inventor of this application.

The prior art disclosed a safety syringe including: a hollow needle (2) preliminarily held in a rigid blocking disk (4) embedded in a rear disk socket (135) perpendicularly formed in a flexible plug (13) inserted in a front portion of the syringe (1) for injection use having a needle head portion (23) formed on a rear portion of the needle (2), and a plunger (31) slidably held in the syringe (1) for boosting a liquid medicine in the syringe to be injected into a patient through the hollow needle (2) having a needle-head socket (32) recessed in the plunger (31) to be engageable with the needle head portion (23) for pushing the needle head portion of the needle (2) frontwardly to drive the rigid blocking disk (4) frontwardly to engage the blocking disk (4) into a front disk socket (137) which is normally inclinedly formed in the flexible plug (13), whereby upon a retraction of the plunger (31) and the needle (2) with the needle head portion (23) received in and coupled to the plunger (31) into the syringe (1) to disengage the needle (2) from the rigid disk (4), the flexible plug (13) will restore the front socket (137) and the rigid disk (4) embedded in the front socket (137) to be inclinedly positioned in the plug (13), thereby blocking an outward protruding of the needle (2) retracted in the syringe (1) for preventing its injury or infectious contamination to the surroundings.

However, the safety syringe of the prior art may still has the following drawbacks:

1. Since the blocking disk member 4 is made as a shallow disk, the central through hole 41 of the block disk member 4 can only be biased for a small oblique angle, which may still be accidentally inserted by an outwardly protruding of the needle (2) already retracted in the syringe (1) to lose its safety meaning.
2. The shallow blocking member 4 is made as a circular disk without having any grip or handle, thereby being difficultly mounted into the first (rear) socket 135 in the plug 13 during the syringe production.

It is therefore expected to further disclose a safety syringe which can be retracted into the syringe in a safer way and will be easily assembled in a factory production.

SUMMARY OF THE INVENTION

The object of the present invention is to provide a safety syringe including a hollow needle for injection use preliminarily held in a rigid blocking bulb generally conical shaped or truncated cone shaped having an elongate stem portion protruding rearwardly from the bulb embedded in a rear bulb socket perpendicularly formed in a flexible plug inserted in a front portion of the syringe having a needle head portion formed on a rear portion of the needle, and a plunger slidably held in the syringe for boosting a liquid medicine in the syringe to be injected into a patient through the hollow needle having a needle-head socket recessed in the plunger to be engageable with the needle head portion to drive and move the rigid blocking bulb frontwardly into a front bulb socket which is normally inclinedly formed in the flexible plug and will be operatively biased perpendicularly in the plug when almost exhausting the liquid in the syringe when finishing the injection, whereby upon a retraction of the plunger and the needle coupled to the plunger rearwardly into the syringe, the elongate stem portion of the rigid bulb will be greatly obliquely biased in a larger angle by the front bulb socket of the plug to be much inclinedly positioned for efficiently blocking an outward protruding of the needle retracted in the syringe for really preventing an injury or infectious contamination to the surroundings as caused by the needle.

BRIEF DESCRIPTION OF THE DRAWINGS

FIG. 1 is an illustration showing the present invention before injection.

FIG. 1a is a sectional drawing of a flexible plug of the present invention.

FIG. 2 is an illustration showing the present invention when finishing the injection.

DETAILED DESCRIPTION

Figure 4:
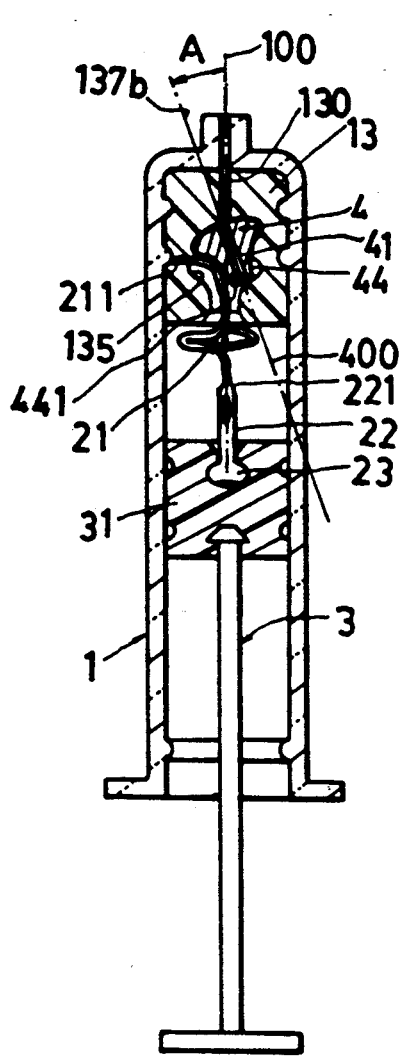
FIG. 4 shows a blocking effect for retarding an outwardly protruding needle in accordance with the present invention.

As shown in FIGS. 1-5, the present invention comprises: a syringe means 1, a hollow needle 2, a plunger means 3, and a rigid blocking bulb 4 movably held in the syringe means 1.

The syringe means 1 includes: a syringe cylinder 11 having a hollow bore portion 10 defined in the syringe cylinder 11 and a syringe axis 100 longitudinally existing in a central portion of the syringe cylinder 11 having a plurality of annular extension rings 111 circumferentially formed in an inner front portion inside the cylinder 11, a sleeve portion 12 protruded frontwardly from the syringe cylinder 11 having a sleeve hole 121 formed in the sleeve portion 12 for holding a needle portion 21 of the hollow needle 2 in the sleeve hole 121, a flexible plug 13 preferably made of soft, flexible elastomer materials inserted in the front portion inside the cylinder 11 having a central hole 130 for passing the needle portion 21 therethrough, a cylindrical portion 131 having a plurality of annular grooves 132 circumferentially formed on the cylindrical portion 131 engageable with the extension rings 111 in the cylinder 11 for fixing the plug 13 in the cylinder 11, a first bulb socket 135 perpendicularly formed in a rear portion of the plug 13 and communicating with a plug guiding port 134 tapered frontwardly from a plug rear surface 133, and a second bulb socket 137 normally inclinedly formed in a front portion of the plug 13 communicating with the first bulb socket 135 through a throat portion 136 formed between the two bulb sockets 135, 137, of which either bulb socket 135 or 137 is operatively engageable with the rigid blocking bulb 4, and a syringe handle 14 formed on a rear end portion of the cylinder 11.

As shown in FIG. 1a, the flexible plug 13 includes the first bulb socket 135 having a longitudinal section generally elliptic shaped and having a first socket center 135c intersected by a first transverse axis 135a, and a first conjugate axis 135b which is normally aligned with the syringe axis 100, thereby orienting the first transverse axis 135a to be normally perpendicular to the syringe axis 100.

The second bulb socket 137 has a longitudinal section generally elliptic and having a second socket center 137c intersected by a second transverse axis 137a, and a second conjugate axis 137b which defines an acute angle A with the syringe axis 100 and is unaligned with the syringe axis 100, thereby normally orienting the second transverse axis 137a inclinedly in the plug 13. The sockets 135, 137 each may have a longitudinal section of elliptical shape, triangular shape or other suitable shapes; or may be formed as truncated-cone shape.

The rigid blocking bulb 4 is made of rigid plastic or other rigid, hard materials insertable in either socket 135 or 137 in the soft flexible plug 13, and is preferably formed as a conical or truncated-cone shape including a bulb base portion 40 and an elongate stem portion 44 tapered or contracted rearwardly from the bulb base portion 40 to be engageable with either bulb socket 135 or 137 in the plug 13 with the bulb base portion 40 having a longitudinally section of elliptical shape, having a through hole 41 defining a bulb axis 400 longitudinally formed in a central portion through the blocking bulb 4 for passing the needle portion 21 of the hollow needle 2 therethrough, a bulb base center 420 intersected by a transverse bulb axis 43 and a conjugate bulb axis 42 existing in a longitudinal center line of the base portion 40 operatively aligned with the syringe axis 100 and a needle axis 200 of the needle 2 when the bulb 4 is normally held in the first bulb socket 135 in the plug 13 and the hollow needle 2 is longitudinally held in the plug 13 ready for injecting a liquid medicine filled in the bore portion 10 of the syringe cylinder 11 as shown in FIG. 1.

A rear bulb surface 441 of the bulb stem portion 44 can be matched with a shoulder portion 221 formed in a front surface of a needle shank portion 22 of the needle 2 to be forwardly driven by the needle shank portion 22 and needle head portion 23 from FIG. 1 to FIG. 2.

The rigid blocking bulb 4 as held on the needle portion 21 to be limited by the shank portion 22 (shoulder portion 221) of the needle is operatively thrusted from the first bulb socket 135 into the second bulb socket 137 through the throat portion 136 between the two bulb sockets 135, 137, with the throat portion 136 defining a diameter smaller than a length of the transverse axis 135a or 137a of any said bulb socket 135, 137.

The hollow needle 2 includes: a needle portion 21 protruding outwardly through the sleeve hole 121 of the syringe means 1 having a tip end 211 formed on an outermost end of the needle, a shank portion 22 connected with the needle portion 21 with a shoulder portion 221 normally contacted with the rear bulb surface 441 of the stem portion 44 of the blocking bulb 4 with a rear end portion of the needle portion 21 inserted in the bulb 4 normally held in the plug 13 for normal injection of the syringe means 1, a needle head portion 23 formed on a rear portion of the shank portion 22 normally protruding rearwardly beyond a plug rear surface 133 to be engageable with a needle-head socket 32 formed in the plunger means 3 having an injection hole 231 formed in the needle head portion 23 communicating with a needle hole 20 formed through the hollow needle 2, a needle axis 200 longitudinally existing in a central portion of the needle 2 normally aligned with the syringe axis 100 when held in the plug 13 for normal injection purpose as shown in FIG. 1, and at least a venting slot 24 formed in the shank portion 22 adjacent to the needle head portion 23 for venting air outwardly through the needle hole 20 of the hollow needle.

The needle head portion 23 of the hollow needle 2 may be formed as elliptic shape to be engaged with an elliptical socket 32 formed in the plunger means 3, but not limited in this invention.

The plunger means 3 includes: a plunger 31 reciprocatively held in the syringe cylinder 11, the needle head socket 32 recessed in a front end portion of the plunger 31 operatively engageable with the needle head portion 23 having a plunger guiding port 33 tapered rearwardly from a plunger front surface 310 for communicating with the needle-head socket 32 for engageably receiving and coupling the needle head portion 23 when finishing the injection for a retraction of the needle 2 as coupled to the plunger 31 into the syringe cylinder 11, a plunger rod 35 having a coupling member 36 engaged with a rear recess 34 formed in the plunger 31 for coupling the plunger 31 on the rod 35 and a plunger handle 37 for pushing the plunger 31 for boosting liquid medicine in the syringe cylinder 11 for injection use. The needle head socket 32 has a socket center aligned with a plunger axis 300 which is aligned with the syringe axis 100 and longitudinally formed in a center line of the plunger means, and projectively aligned with a needle head center 230 of the needle head portion 23 for a snug engagement of the needle head portion 23 with the needle-head socket 32 of the plunger 31 for coupling the needle 2 to the plunger means 3 which is operatively pushed frontwardly for movably driving the rigid blocking bulb 4 from a first bulb socket 135 to a second bulb socket 137 when finishing the injection (FIG. 2) and is then retracted to pull the needle 2 coupled on the plunger 31 to be stored into the syringe cylinder 11, whereby the rigid blocking bulb 4 will then be automatically restored by the flexible plug 13 to be inclinedly positioned in the plug 13 and the central through hole 41 of the blocking bulb 4 is then unaligned with the needle axis 200 and syringe axis 100 as shown in FIG. 3 for blocking an outward protrusion of the retracted needle portion 21 for preventing a sting injury or infectious contamination by the needle 2.

As shown in FIG. 4, a further outward protrusion of the needle 2 will be automatically blocked by the blocking bulb 4 by bending, deforming or poking the needle tip end 211 into the plug 3 to be obstructed by the syringe cylinder 11 (FIG. 4) which can not be pushed outwardly from the syringe cylinder 11 for a better safety and hygienic protection.

Figure 3:
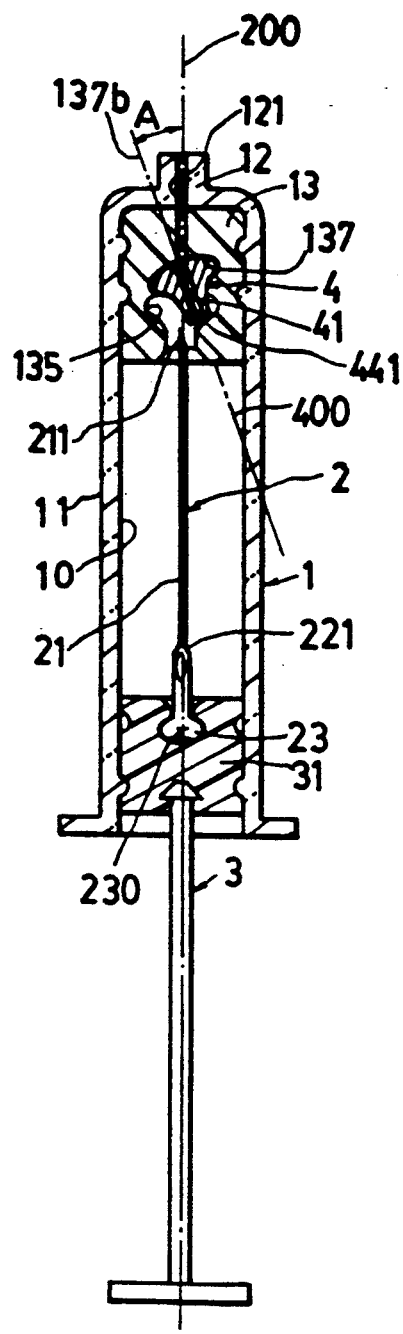
FIG. 3 shows the present invention having a needle retracted in a syringe.

After the retraction of the needle 2 coupled to the plunger 31 into the syringe cylinder 11 as shown in FIG. 3, the flexible plug 13 will be automatically restored by its self elasticity to restore the second socket 137, from its flattened state (blocking bulb 4 perpendicular to the axis 100) as pressurized by the plunger means 3 as shown in FIG. 2, to be an inclined situation wherein the rigid hard blocking bulb 4 will be restored to be inclinedly positioned (FIG. 3), thereby blocking the unexpected outwardly protrusion of a retracted needle 2 as shown in FIG. 4.

Figure 5:
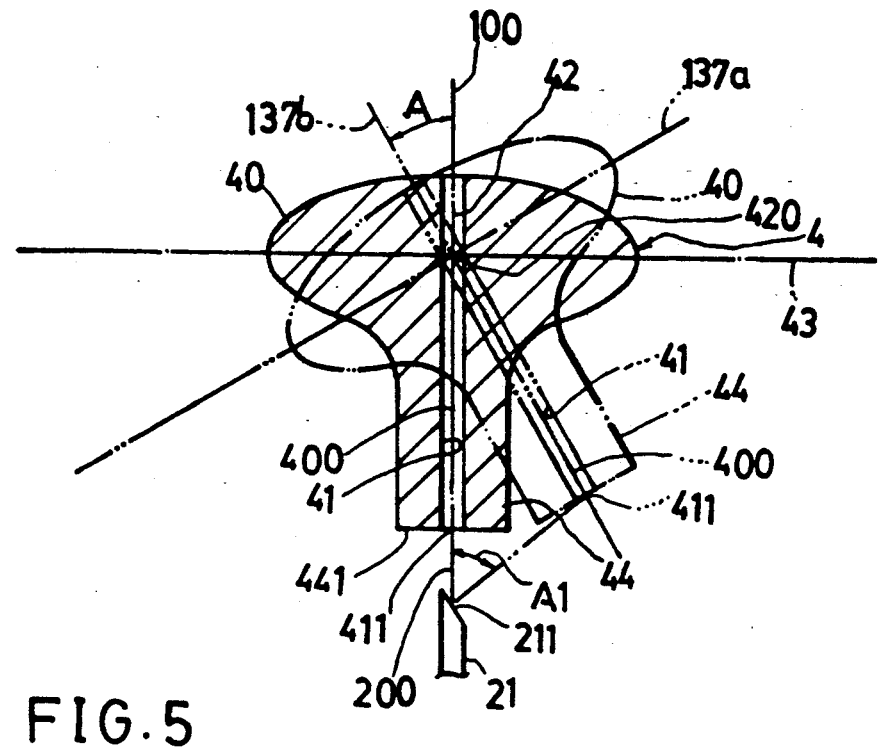
FIG. 5 shows a rigid blocking bulb of the present invention.
Figure 6:
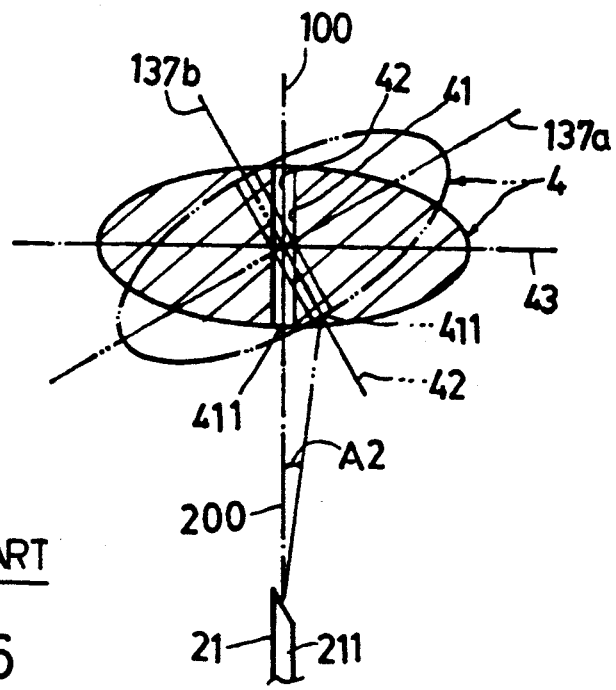
FIG. 6 shows a rigid blocking disk member of the prior art.

As shown in FIG. 5, the bulb 4 of this application includes the elongate stem portion 44 protruding rearwardly from the bulb base portion 40 to thereby greatly increase a deviation angle A1, wider than a smaller angle A2 as effected by the "shallow" blocking disk member of the prior art (U.S. Ser. No. 07/983,144) as shown in FIG. 6, so that it will be more difficult to protrude the retracted needle tip end portion 211 of this application outwardly through an "inlet port" or rear port 411 of the central through hole 41 of the blocking bulb 4, to be safer than the prior art as shown in FIG. 6 since the deviation angle A1 of this application is much increased than that A2 of the prior art.

Meanwhile, the stem portion 44 of the bulb of this application can be easily grasped for a smoothly mounting of the bulb 4 with the needle 2 to be embedded into the socket 135 for an easier assembly and production of this application than the prior art.

I claim:

1. A safety syringe comprising:
   a syringe means having a flexible plug inserted in a front portion inside a syringe cylinder of said syringe means defining a syringe axis longitudinally existing in a central portion in said syringe means, said flexible plug having a first bulb socket formed in a rear portion in said plug normally perpendicular to said syringe axis, and a second bulb socket formed in a front portion in said plug and communicating with said first socket and normally inclinedly positioned in said plug;
   a rigid blocking bulb generally conical shaped, including a bulb base portion and an elongate stem portion tapered rearwardly from said bulb base portion having a central through hole longitudinally formed through said bulb, normally engageably held in said first bulb socket of said plug and operatively moved into said second bulb socket to be engageable with said second bulb socket; and
   a hollow needle normally held in said rigid blocking bulb and in said plug defining a needle axis normally aligned with said syringe axis, and operatively thrusted frontwardly as urged by a plunger means reciprocatively held in said syringe means to be moved frontwardly towards said second bulb socket when finishing an injection, said needle being operatively coupled to said plunger means when finishing the injection by engaging a needle head portion formed on a rear end portion of said hollow needle with a needle-head socket recessed in said plunger means, whereby upon a retraction of said needle into said syringe cylinder, said flexible plug will automatically restore said second bulb socket to inclinedly orient said rigid blocking bulb to unalign the central through hole of said bulb from said hollow needle to greatly deviate a positioning of a rear port of the through hole, formed in a rear stem surface of said stem portion of said bulb, from the syringe axis and the needle axis for effectively preventing an outward protrusion of the needle as retracted in said syringe cylinder.

2. A safety syringe according to claim 1, wherein each said first and second bulb socket has a longitudinal section of elliptical shape engageable with an elliptically shaped bulb base portion of said blocking bulb.

3. A safety syringe according to claim 1, wherein each said first and second bulb socket has a longitudinal section of triangular shape, engageable with said blocking bulb generally conical shaped.

4. A safety syringe according to claim 2, wherein said second bulb socket defines a second transverse axis and a second conjugate axis perpendicular to said second transverse axis, with said second conjugate axis of said second bulb socket operatively aligned with a conjugate bulb axis of the elliptically shaped bulb base portion of said blocking bulb having defining a transverse bulb axis perpendicular to said conjugate bulb axis.

* * * * *